(12) United States Patent
Kwon et al.

(10) Patent No.: US 11,440,787 B2
(45) Date of Patent: Sep. 13, 2022

(54) REFRIGERATOR HAVING DISPENSER

(71) Applicant: LG ELECTRONICS INC., Seoul (KR)

(72) Inventors: O Min Kwon, Seoul (KR); Hyungkyu Park, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 17/356,051

(22) Filed: Jun. 23, 2021

(65) Prior Publication Data

US 2021/0316981 A1 Oct. 14, 2021

Related U.S. Application Data

(63) Continuation of application No. 16/551,027, filed on Aug. 26, 2019, now Pat. No. 11,046,571.

(30) Foreign Application Priority Data

Feb. 1, 2019 (KR) .................. 10-2019-0014116

(51) Int. Cl.
*B67D 1/07* (2006.01)
*F25D 23/02* (2006.01)
*B67D 1/00* (2006.01)
*B67D 1/08* (2006.01)
*C02F 1/32* (2006.01)
(Continued)

(52) U.S. Cl.
CPC .............. *B67D 1/07* (2013.01); *B67D 1/0014* (2013.01); *B67D 1/0887* (2013.01); *C02F 1/325* (2013.01); *F25D 23/028* (2013.01); *F25D 23/126* (2013.01); *F25D 27/00* (2013.01); *B67D 2001/075* (2013.01);
(Continued)

(58) Field of Classification Search
CPC ...... B67D 1/07; B67D 1/0014; B67D 1/0887; B67D 2001/075; B67D 2201/3222; B67D 2210/00015; C02F 1/325; C02F 2201/3222; C02F 2307/10; F25D 23/028; F25D 27/00; F25D 23/126; F25D 2327/001

See application file for complete search history.

(56) References Cited

U.S. PATENT DOCUMENTS

| 2019/0382254 A1 | 12/2019 | Kim et al. | |
| 2019/0389712 A1 | 12/2019 | Kim et al. | |
| 2020/0115212 A1* | 4/2020 | Kim | A61L 2/10 |

FOREIGN PATENT DOCUMENTS

| KR | 10-2009-0075068 | 7/2009 |
| KR | 10-2018-0070354 | 6/2018 |

(Continued)

OTHER PUBLICATIONS

European Search Report dated Feb. 28, 2020 issued in EP Application No. 19194405.7.

(Continued)

*Primary Examiner* — Jason K Niesz
(74) *Attorney, Agent, or Firm* — KED & Associates, LLP

(57) ABSTRACT

A refrigerator may be provided with a dispenser which includes a nozzle pipe; a light source that radiates ultraviolet light from one end of the nozzle pipe to an inner space of the nozzle pipe, a window that is provided between the one end of the nozzle pipe and the light source, and a liquid supplying hose barb connected to the nozzle pipe via an elbow. Liquid exiting the elbow swirls as ultraviolet light is irradiated onto the liquid.

11 Claims, 10 Drawing Sheets

(51) Int. Cl.
*F25D 23/12* (2006.01)
*F25D 27/00* (2006.01)

(52) U.S. Cl.
CPC ............... *B67D 2210/00015* (2013.01); *C02F 2201/3222* (2013.01); *C02F 2307/10* (2013.01); *F25D 2327/001* (2013.01)

(56) References Cited

FOREIGN PATENT DOCUMENTS

| | | |
|---|---|---|
| KR | 10-2018-0070355 | 6/2018 |
| KR | 10-2018-0085145 | 7/2018 |
| WO | WO 2018/111056 | 6/2018 |
| WO | WO 2018/111057 | 6/2018 |
| WO | WO 2018/124668 | 7/2018 |

OTHER PUBLICATIONS

United States Office Action dated Oct. 7, 2020 issued in co-pending related U.S. Appl. No. 16/551,027.
United States Notice of Allowance dated Mar. 4, 2021 issued in co-pending related U.S. Appl. No. 16/551,027.

* cited by examiner

REFRIGERATOR HAVING DISPENSER

CROSS-REFERENCE TO RELATED APPLICATION(S)

This application is a Continuation Application of prior U.S. patent application Ser. No. 16/551,027 filed Aug. 26, 2019, which claims priority under 35 U.S.C. § 119 to Korean Patent Application No. 10-2019-0014116 filed in Korea on Feb. 1, 2019, and the disclosure of which is incorporated herein by reference in its entirety.

BACKGROUND

1. Field

The present disclosure relates to a refrigerator having a dispenser.

2. Background

A dispenser that may dispense water and ice may be installed in the door of a refrigerator for user convenience. In stand alone water purifiers, enough space is allocated for a dispenser. However, in a refrigerator having a water purifier therein, a dispenser may need to have a compact structure because the depth of the door may be narrow in the front-rear direction of the door.

Additionally, a pipe or a hose through which purified water flows may become contaminated, or bacteria may breed in the pipe or hose as time passes. The pipe or hose may need to be replaced with a new one periodically. Accordingly, the dispenser in the door of a refrigerator may have a structure that may be readily maintained and repaired.

The cycle of maintaining and repairing the dispenser may be lengthened to reduce the burden of maintaining and repairing the dispenser. In patent document 1, structures of a water purifier and a water discharging member of a dispenser installed in the general water purifier are disclosed. The water purifier periodically sterilizes the water discharging member that is placed at a boundary between the inner space and outer space of the water purifier using ultraviolet light.

However, the water discharging member is not adequate for the dispenser of a refrigerator that may not have enough space required for installing the water discharging member. A ultraviolet light-emitting diode (UV LED) that radiates ultraviolet light should not be exposed to water. Accordingly, the UV LED that is installed in the water discharging member should be prevented from contacting water. Further, the water discharging member needs to have a structure that may be easily manufactured and that may definitely seal the UV LED to prevent water from invading the UV LED.

Ultraviolet light that is radiated from a UV LED has a peak wavelength adequate for eradicating bacteria that inhabit in the pipe through which purified water flows. Further, ultraviolet light is preferably radiated onto all the inner wall surfaces of the water discharging member, which contact water.

(Patent Document 1) Korean Laid-Open Publication No. 10-2018-0085145

BRIEF DESCRIPTION OF THE DRAWINGS

Embodiments will be described in detail with reference to the following drawings in which like reference numerals refer to like elements, and wherein.

DETAILED DESCRIPTION

Figure 1:
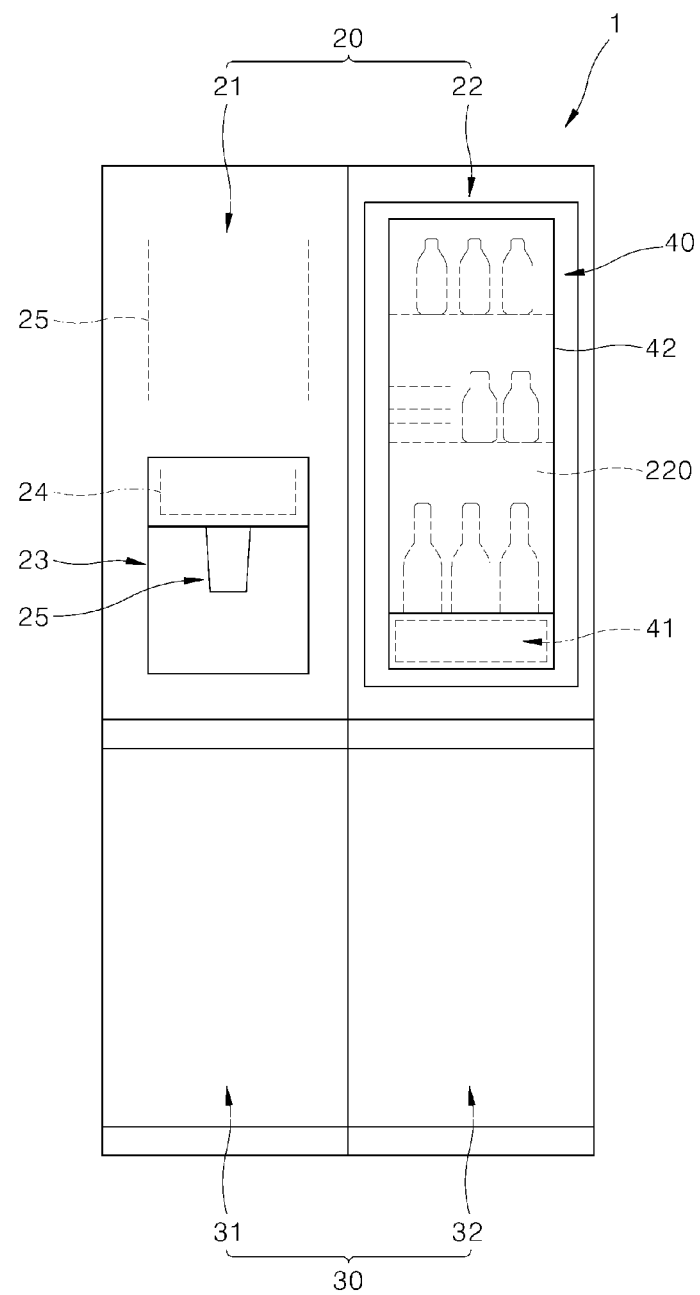
FIG. 1 is a front view illustrating a refrigerator according to an implementation.

Referring to FIG. 1, the outer shape of a refrigerator 1 according to implementations may be defined by a cabinet that forms a storage space, and doors 20, 30 that open and close the storage space. The inside of the cabinet may be divided into an upper portion and a lower portion, and a refrigerating compartment may be formed in the upper portion of the cabinet while a freezer compartment may be formed in the lower portion of the cabinet. The inside of the cabinet may also be divided into a left portion and a right portion, and a refrigerating compartment and a freezer compartment respectively may be formed in the left portion and the right portion of the cabinet.

The door may include a refrigerating compartment door 20 and a freezer compartment door 30. The refrigerating compartment door 20 and freezer compartment door 30 may each be rotatably installed and may open and close the refrigerating compartment and freezer compartment respectively.

The refrigerating compartment door 20 may include a pair of doors 21, 22 that open and close the refrigerating compartment in the upper portion of the cabinet 10, i.e., a left refrigerating compartment door 21 and a right refrigerating compartment door 22. The freezer compartment door 30 may include a pair of doors 31, 32 that open and close the freezer compartment in the lower portion of the cabinet 10, i.e., the left freezer compartment door 31 and the right freezer compartment door 32. However, implementations of the present disclosure may be applied to a dispenser installed in all types of doors of refrigerators regardless of the shapes and structures of the doors.

The left refrigerating compartment door 21 may include an ice maker 25 on the inner surface thereof. The ice maker 25, which may be a device for making and storing ice by means of automatic water supply, may be provided in a thermally insulated space formed on the rear surface of the left refrigerating compartment door 21.

The left refrigerating compartment door 21 may include a dispenser 23 on the front surface thereof. The dispenser 23 may dispense ice that is made by the ice maker 25, and/or purified water. Ice or water may be dispensed according to an external input of the user.

The second display 24 may show the state where the dispenser 23 and the refrigerator 1 operate and may be used for inputting the operation of the dispenser and the refrigerator. When the right refrigerating compartment door 22 does not include a first display 41, the second display may perform functions of the first display 41.

The right refrigerating compartment door 22 may include an opening 220 at the center thereof, and the opening 220 may include a door basket on the inner side thereof. Additionally, the right refrigerating compartment door 22 may include a sub door 40 that opens and closes the opening 220. One lateral end of the sub door 40 may be rotatably hinge-coupled to the right refrigerating compartment door 22. The user may open and close the sub door 40 to access the door basket.

The opening 220 may include a first display 41 at a lower end of the opening 220. The first display 41 may display an operational state of the refrigerator, and the user may manipulate and input an operation of the refrigerator 1.

The sub door 40 may include a visible part 42 that is used to see the inside of the door basket. Thus, with the sub door 40 closed, the inside of the door basket may be seen through the visible part 42. A refrigerator without the sub door 40 may not include the first display 41, and the second display 24 may perform functions of the first display 41.

Figure 2:
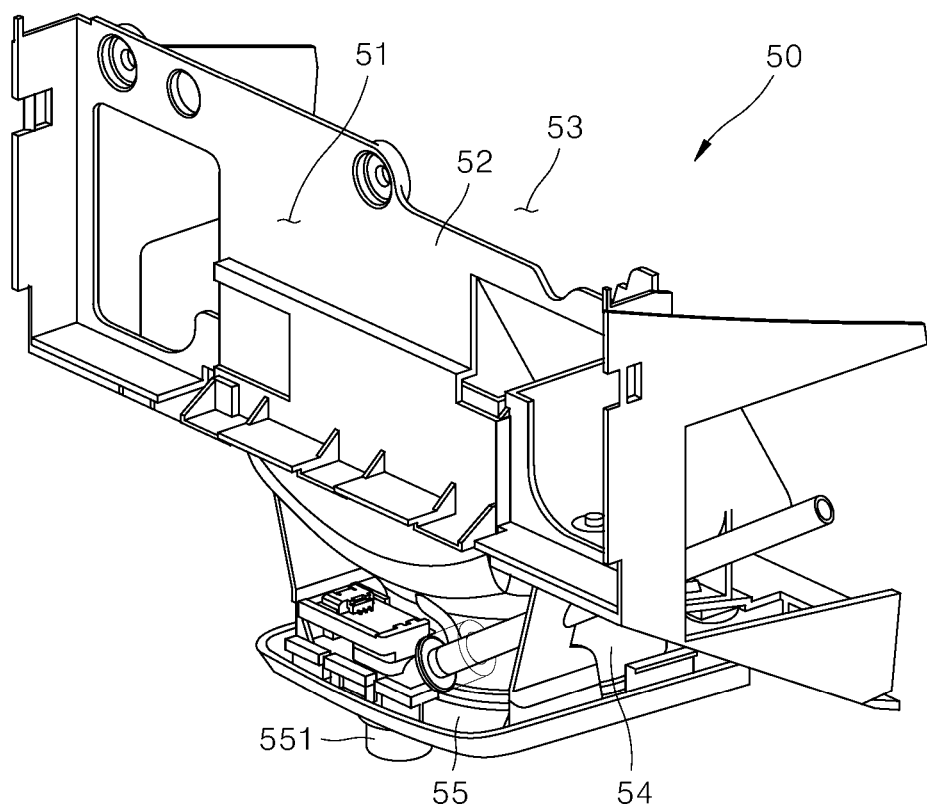
FIG. 2 is a perspective view illustrating a dispenser housing that is installed in a door of the refrigerator.
Figure 3:
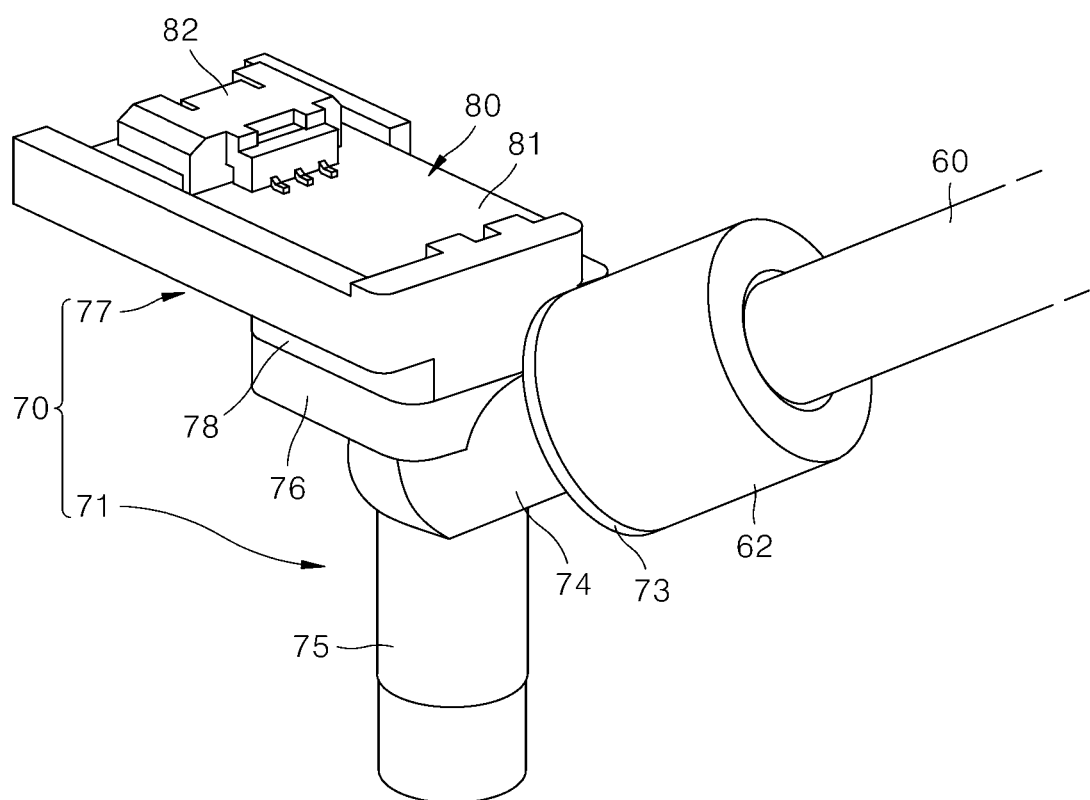
FIG. 3 is an enlarged perspective view illustrating a water discharging member that is installed in the dispenser housing in FIG. 2.
Figure 4:
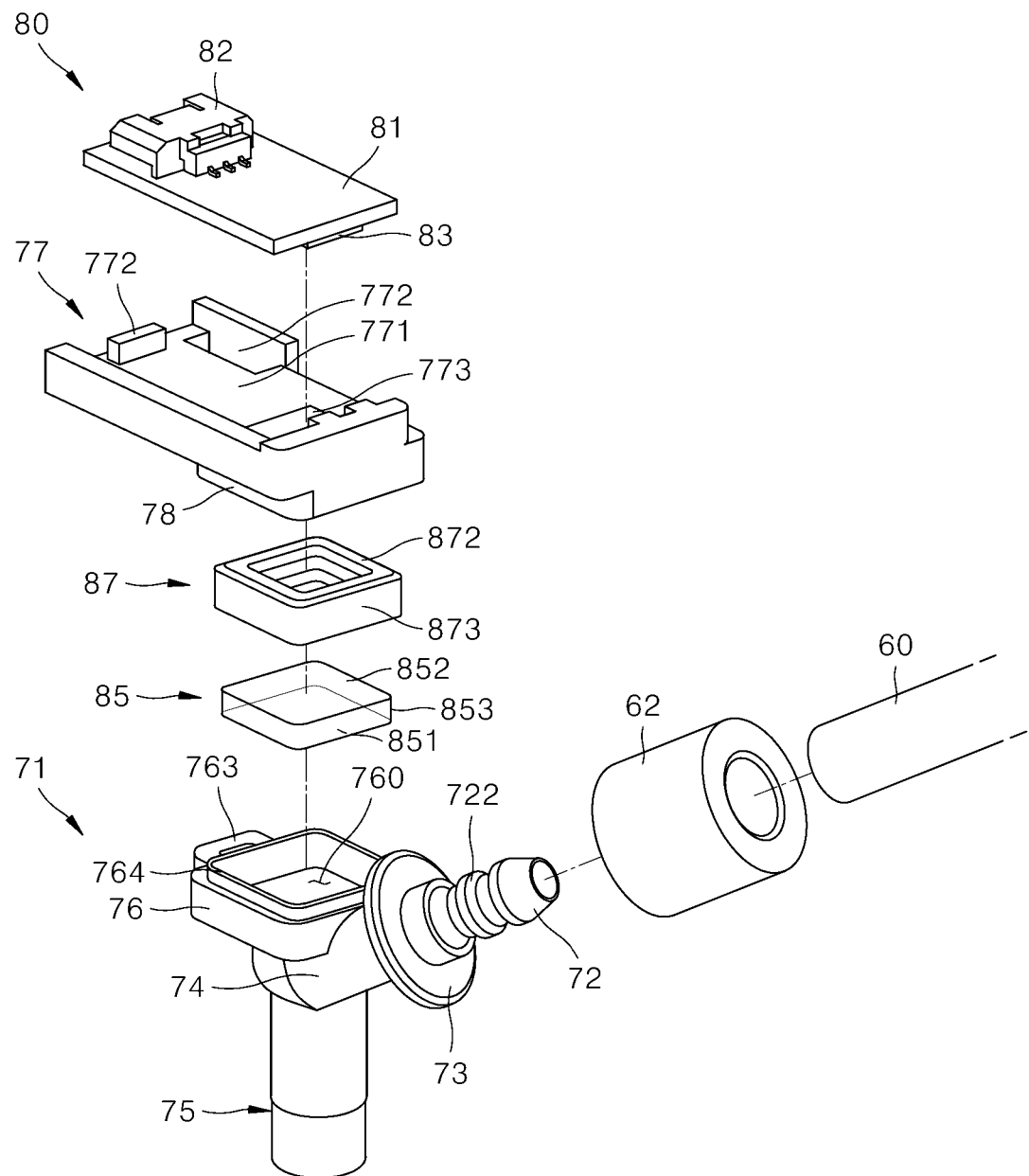
FIG. 4 is an exploded perspective view illustrating the water discharging member in FIG. 3.
Figure 5:
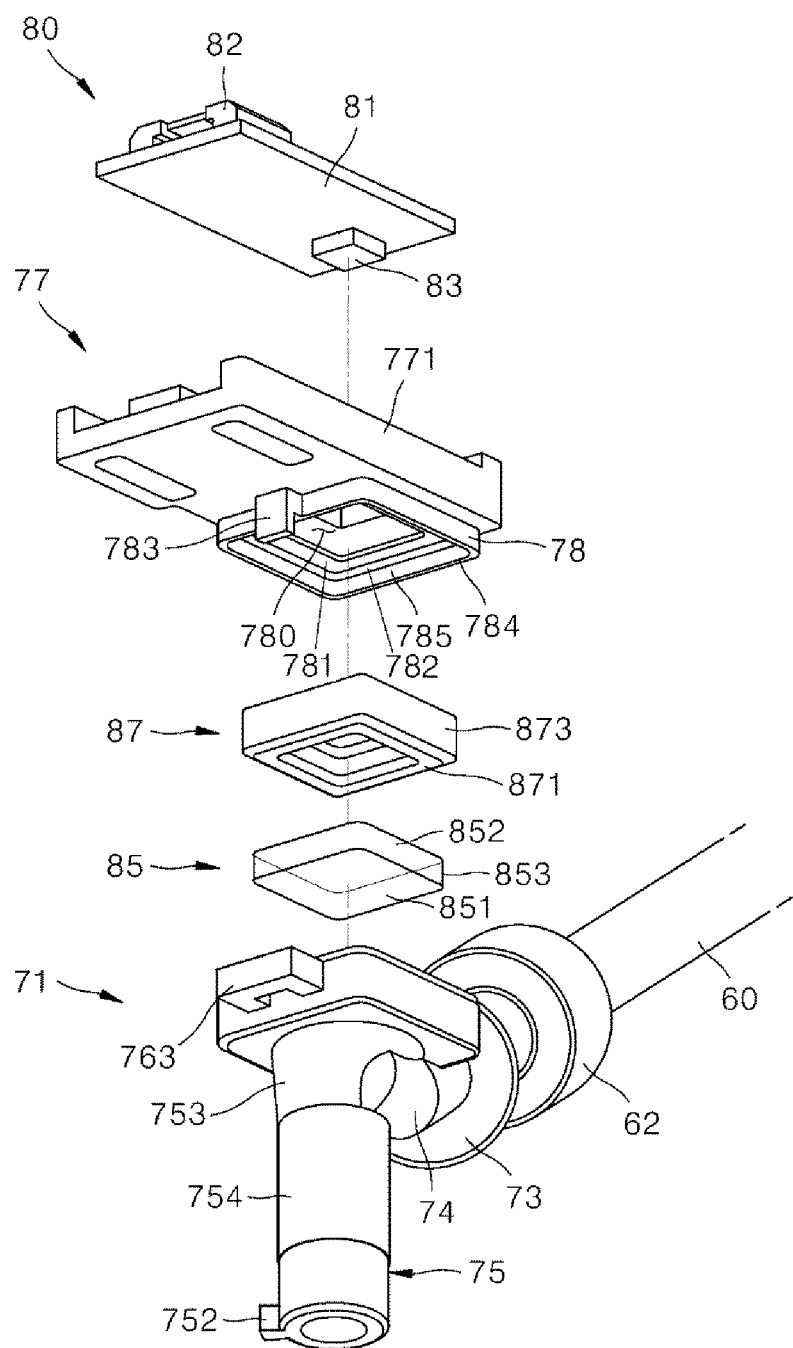
FIG. 5 is an exploded perspective view illustrating the water discharging member in FIG. 3 that is seen from a lower portion thereof.
Figure 6:
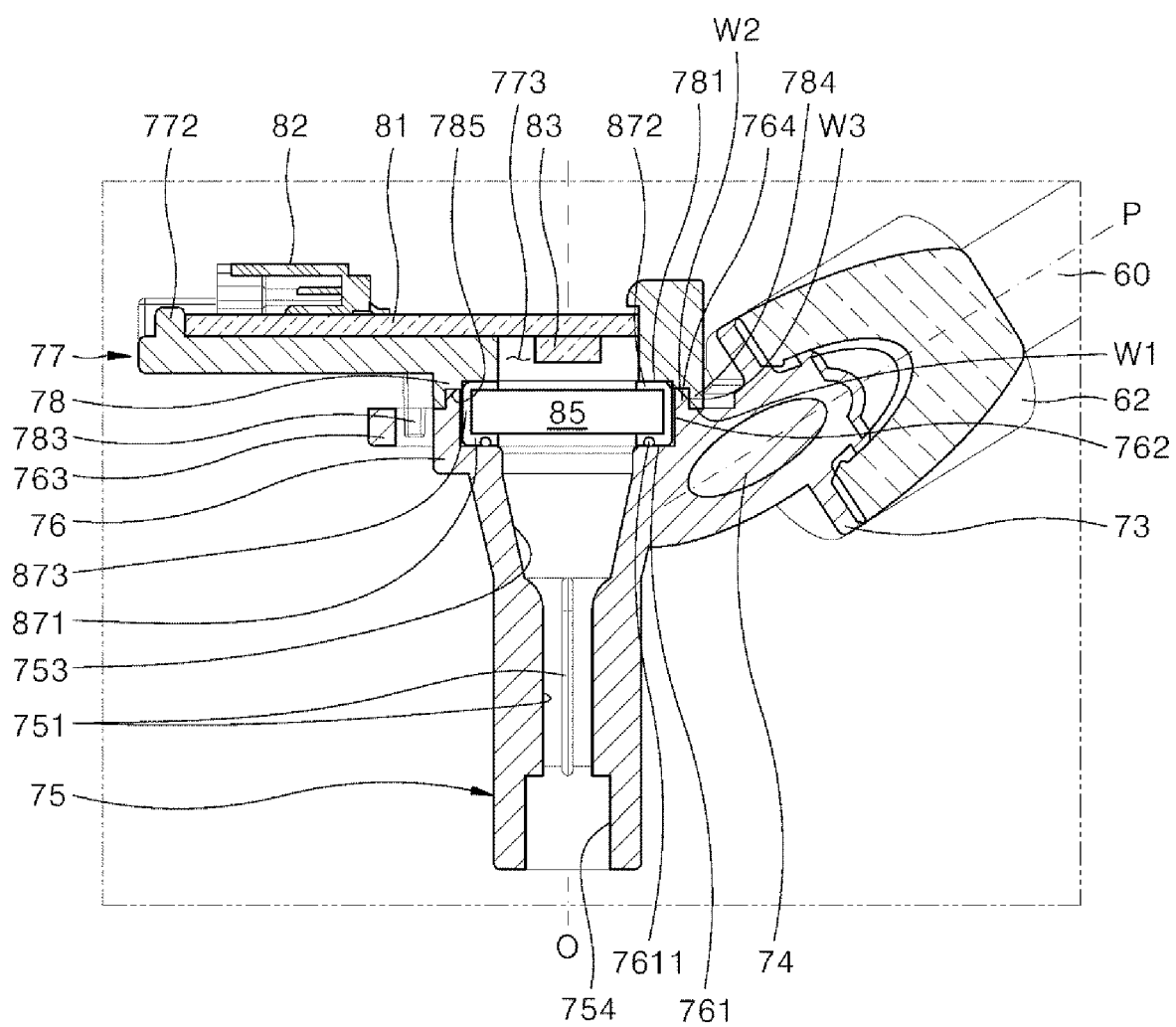
FIG. 6 is a lateral sectional view illustrating the water discharging member in FIG. 3.

Referring to FIG. 2, the dispenser 23 may include a dispenser housing 50 that is installed in the door 21. The dispenser housing 50 may include a main-wall member 52 that is parallel with the surface of the door. The second display 24 may be built into a space at the front of the main-wall member 52. An ice-transporting-device installing space 53 in which an ice transporting device is installed may be provided in space at the rear of the main-wall member 52. The ice transporting device may transport ice that is produced and stored by the ice maker 25 to a discharging part (or discharge funnel) 54. The discharge funnel 54 may have a shape the surface area of which becomes narrower toward the lower portion of the discharge funnel 54.

The discharge funnel 54 may include a bottom-surface member 55 that extends horizontally in the lower end portion thereof. The bottom-surface member 55 may include a portion that extends toward the front of the discharge funnel 54, and a nozzle supporting part (or nozzle support tube) 551 may be provided in this portion.

The discharge funnel 54 may be provided further backward than the nozzle support tube 551. Accordingly, the upper space of the nozzle support tube 551 may be narrow and may be larger in the left-right direction than in the front-rear direction.

The nozzle support tube 551 may include a water discharging member 70. The water discharging member 70 may be an outlet through which purified water is discharged. The user may place a container in the lower portion of the discharge funnel 54 of the dispenser to receive ice or place a container in the lower portion of the water discharging member 70 that is arranged in front of the discharge funnel 54 to receive water.

Referring to FIGS. 3 to 7, the water discharging member 70 may connect with a hose 60 that is supplied with water. The hose 60 may connect with a water tank or may directly connect with a faucet via a purifying filter. The end portion of the hose 60 may be fixed to the water discharging member 70 by a clamp 62.

The water discharging member 70 may include a nozzle part (or nozzle) 71 and a light-source installing part (or light-source bracket) 77. The nozzle 71 may discharge water supplied through the hose 60. The light-source bracket 77 may include an ultraviolet-light source 80 that sterilizes the nozzle 71.

The inner space of the nozzle 71 and the light-source bracket 77 may be spatially divided by sealing a sealing member or seal 87. Because water flows in the nozzle 71 and the light-source bracket 77 includes the ultraviolet-light source, the water that flows in the nozzle 71 may not enter the light-source bracket 77. Ultraviolet light radiated from the light source 80 of the light-source bracket 77 may pass through a window or transparent plate 85 and may be radiated into the nozzle 71. The window 85 may alternatively be referred to as a lens.

The nozzle 71 may include a water-supplying-part connecting pipe or barb 72 that connects with the hose 60, a nozzle pipe 75 that connects with the water-supplying-part connecting barb and guides water such that the water is discharged, and a first-portion accommodating part (or window pocket or lower groove) 76 that accommodates at least a part of the window 85 and the seal 87. The window pocket 76 may be a window-lower-portion accommodating part that accommodates lower portions of the window 85 and the seal 87.

The light-source bracket 77 may include a second-portion accommodating part (or seal pocket or upper groove) 78 that connects with the window pocket 76 and that accommodates a second portion of the window 85 and the seal 87. The nozzle 71 and the light-source bracket 77 may be separately manufactured and then coupled.

The water-supplying hose barb 72 may include a concave-convex part (or rib) 722 on an outer surface thereof along the perimeter thereof. The hose 60 may have an inner diameter that is smaller that of an outer diameter of a protruding portion of the rib 722 and may include a material having a certain level of elasticity.

The water-supplying hose barb 72 may be fitted into the hose 60 at an end portion of the hose 60, and, accordingly, the diameter of the hose 60 that faces the protruding portion of the rib 722 may be extended. Additionally, the clamp 62 may be provided around the outer perimeter of the hose 60 and fitted into the water-supplying hose barb 72. The hose 60 may be fitted between the inner circumferential surface of the bore of the clamp 62 and the protruding portion of the rib 722 and strongly compressed.

The water discharging member 70 may be sterilized with ultraviolet light of the light source 80 continuously and/or periodically. Accordingly, the water discharging member 70 may not need to be replaced frequently. Unlike the water discharging member, the hose 60 may need to be replaced frequently. The water-supplying hose barb 72 and the clamp 62 may simply connect and separate the hose 60 and the water discharging member 70 and definitely seal the same.

The water-supplying hose barb 72 may include a flange 73 that radially extends at an inner end of the lengthwise direction thereof. The flange 73 may have a circular shape. The flange 73 may properly regulate a length at which the water-supplying hose barb 72 is inserted into the hose 60. In other words, the user may insert the water-supplying hose barb 72 into the hose 60 until an end portion of the hose 60 contacts the flange 73.

The water-supplying hose barb 72 may be connected to a detouring part (or elbow) 74 with the flange 73 between the water-supplying-part connecting pipe and the detouring part. The water-supplying hose barb 72 may connect with the nozzle 75 through the elbow 74. As in FIG. 7, an axis (P) that passes the center of the water-supplying hose barb 72 and the elbow 74 may be arranged so as not to meet with and to avoid a central axis (O) of the nozzle 75. In other words, the two axes (O, P) may be orthogonal to each other.

Additionally, the axis (P) may be provided outside an inner area of the nozzle 75. The elbow 74 may connect with the nozzle 75 in a way that contacts the perimeter of the nozzle 75, and the inner space of the elbow 74 may connect with the inner space of the nozzle 75 so as to communicate with the same. The axis (P) may be inclined backward and upward from the nozzle 75.

The elbow 74 may allow the water supplied through the water-supplying hose barb 72 to the nozzle 75 to flow along the perimeter of the inner wall surface of the nozzle 75 like a swirl so as not to be directly discharged toward the center of the nozzle 75. Accordingly, flow of the water discharged out of the water discharging member may be stabilized. Additionally, a below-described laminar flow protrusion 751 may turn the swirl into laminar flow. Thus, water may be stably discharged.

The axis (P) may be inclined with respect to a surface perpendicular to the central axis (O) of the nozzle 75 in the lengthwise direction thereof. In other words, the axis (P) may be inclined downward toward the nozzle 75. A gradient of the axis (P) with respect to the slope may be 20 to 40 degrees. Thus, water may not stagnate in the water-supplying hose barb 72. The gradient of the axis (P) may allow the water supplied through the water-supplying hose barb 72 to be supplied to the nozzle 75 due to the kinetic energy of a downward motion. Water may not be left in the nozzle 75 because of the swirl and the kinetic energy of downward motion.

The nozzle 75 may extend along a vertical direction. The nozzle 75 may include a funnel part 753 and a small diameter part or space 754. The funnel part 753 may be provided in the upper portion of the nozzle 75 while the small diameter part 754 may be provided in the lower portion of the nozzle 75. The small diameter part 754 may connect with a lower portion of the funnel part 753. The funnel part 753 may define a funnel space and the small diameter part 754 may define a small diameter or cylindrical space. The funnel part 753 and small diameter part 754 may alternatively be referred to as first and second portions or sections of the nozzle 75.

The elbow 74 may connect to the funnel part 753. The funnel part 753 may have a shape the inner diameter of which becomes smaller toward the lower portion thereof. Additionally, the funnel part 753 may have a shape the outer diameter of which becomes smaller toward the lower portion thereof.

The small diameter part 754 may have a pipe or cylindrical shape. The outer edge and inner edge of the upper end portion of the small diameter part 754 may have shapes corresponding to those of the outer edge and inner edge of the lower end portion of the funnel part 753.

The funnel part 753 may have a cone or funnel shape while the small diameter part 754 may have a circular pipe shape. The inner diameter and outer diameter of the small diameter part 754 may correspond respectively to the inner diameter and outer diameter of the lower end portion of the funnel part 753.

A laminar flow protrusion or vane 751 that protrudes inward to the center (O) of the small diameter part 754 and that extends in the lengthwise direction of the small diameter part 754 may be provided in the upper portion of the small diameter part 754, i.e., a portion adjacent to the funnel part 753. A plurality of laminar flow protrusions 751 may be radially provided. In implementations, four laminar flow protrusions 751 may be provided at 90-degree intervals.

The water supplied from the water-supplying hose barb 72 to the nozzle 75 through the elbow 74 may move downward while hovering in the funnel part 753 and may be collected in the small diameter part 754. The water coming into the small diameter part 754 may be turned into stable laminar flow by the laminar flow protrusion 751.

The laminar flow protrusion 751 may be provided near the upper end portion of the small diameter part 754 but may not extend to the lower end portion of the small diameter part 754. Accordingly, water that separately flows by the laminar flow protrusion 751 may be gathered again in the lower end portion of the small diameter part 754 and discharged, thereby making it possible to stabilize flow of water that is supplied to the user through the other end of the lower end portion of the nozzle pipe 75.

The swirling flow may lengthen a period of time for which the water flows in the nozzle pipe 75. Water may be directly sterilized when the light source 80 is turned on while water is discharged.

The window pocket 76 may connect to the upper portion of the nozzle 75, i.e., the upper portion of the funnel part 753. The window pocket 76 may define a square cross section including an inner cross section of the upper end portion of the funnel part 753.

The window pocket 76 may include a window-bottom-surface supporting surface 761 that extends outward from the upper end portion of the funnel part 753, and a window-lateral-surface-lower-portion supporting surface 762 that extends upward from the outer edge of the window-bottom-surface supporting surface 761. The window-bottom-surface supporting part 761 (first-surface supporting surface) may support a first surface 851 (lower surface) of the window member 85 While the window-lateral-surface-lower-portion supporting surface 762 (lateral-surface-first-portion supporting surface) may support the lower portion of the lateral surface 853 of the window member 85.

Figure 7:
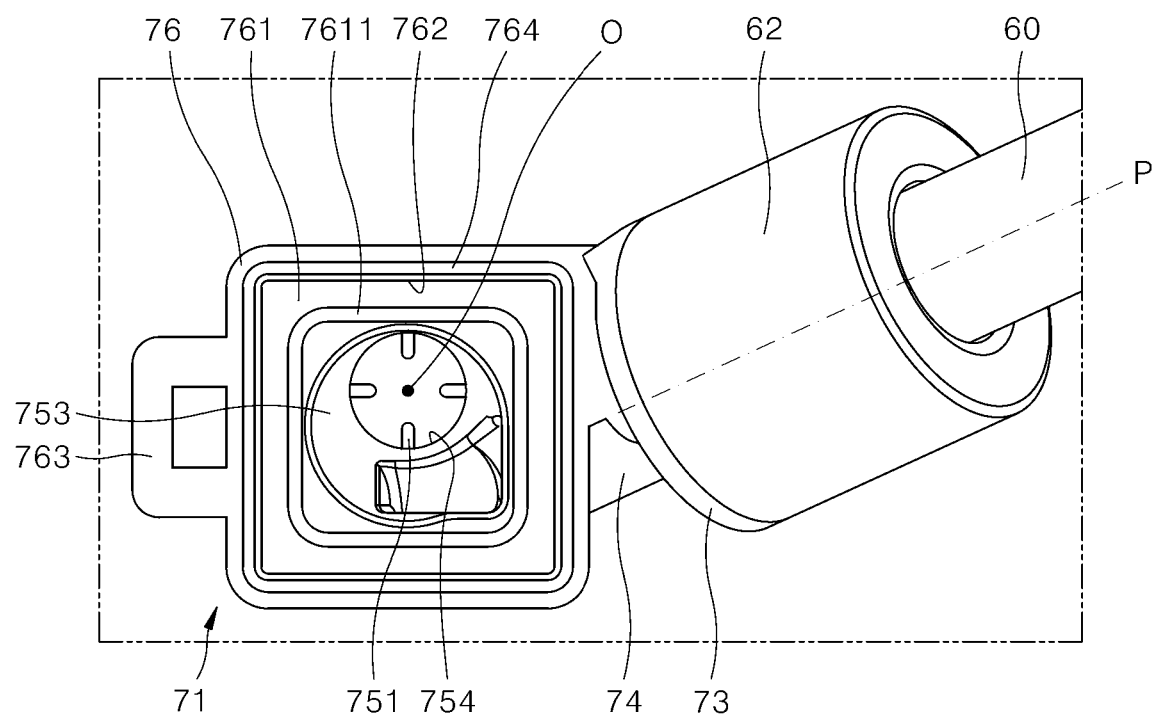
FIG. 7 is a plan view illustrating the water discharging member in FIG. 3 in which a light-source installing part, a window member, and a sealing member are omitted.
Figure 8:
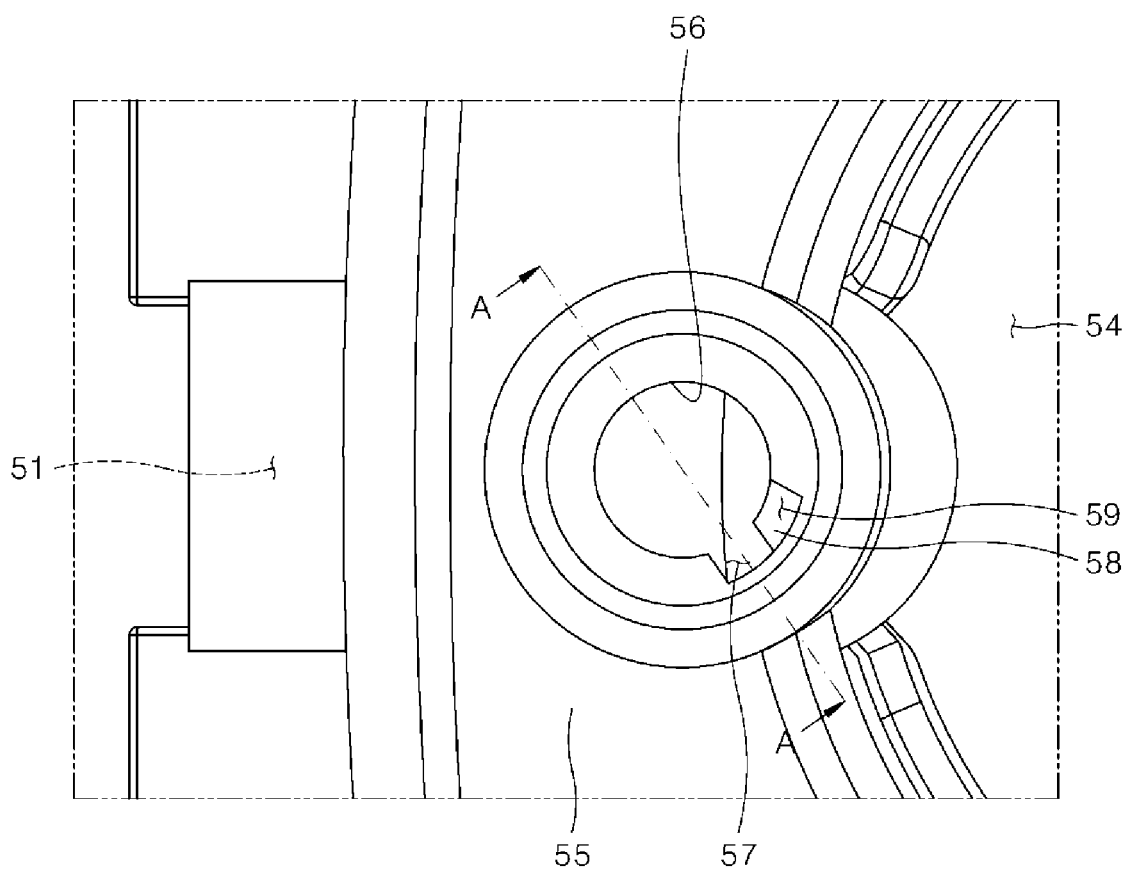
FIG. 8 is an enlarged bottom view illustrating a portion of a dispenser housing in which a water discharging member is installed.
Figure 9:
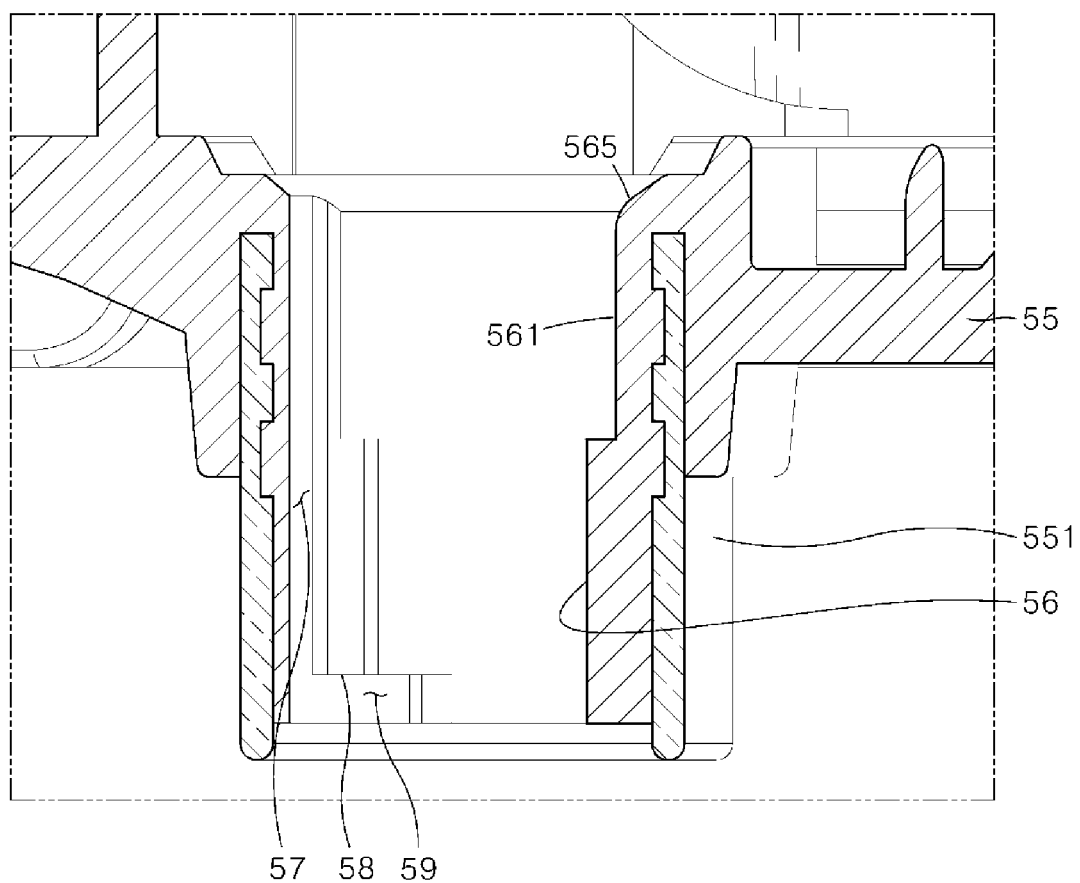
FIG. 9 is a sectional view illustrating a portion cut along line A-A in FIG. 8.
Figure 10:
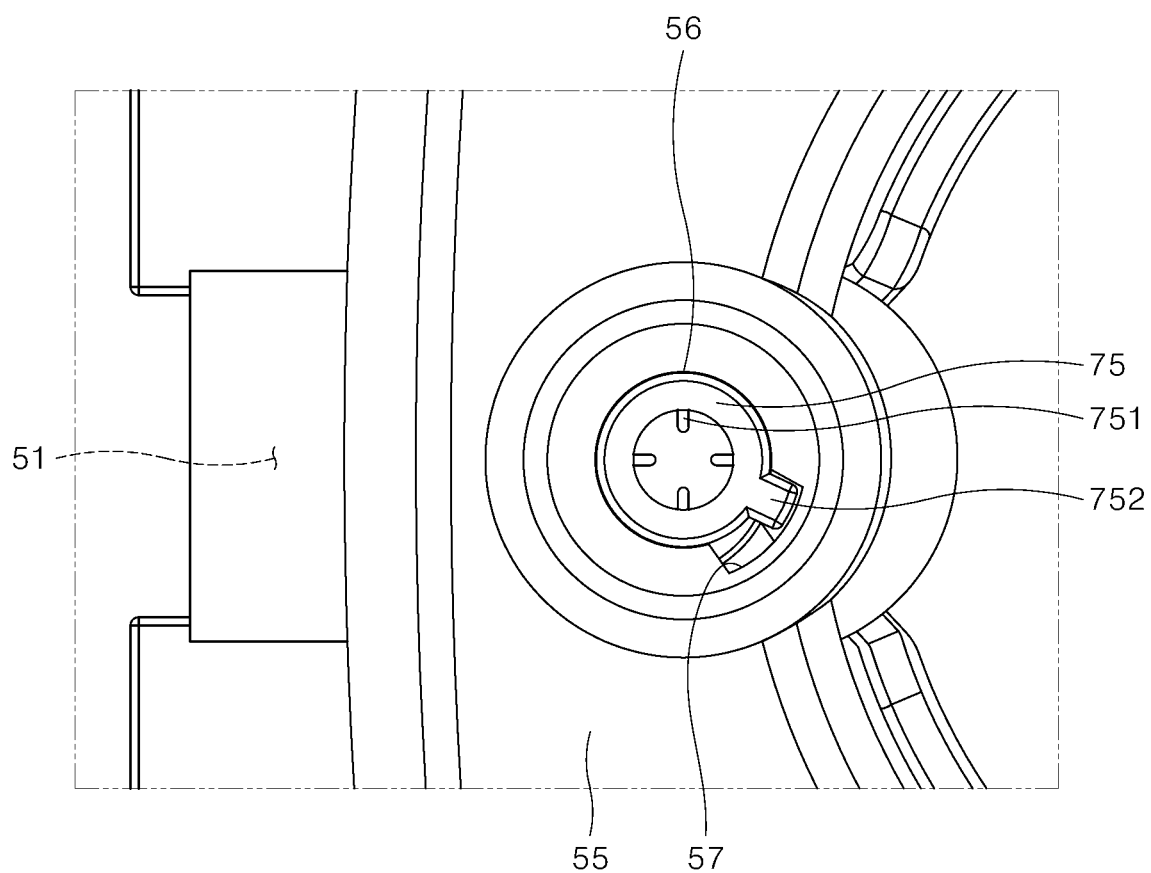
FIG. 10 is an enlarged bottom view illustrating a dispenser housing in which a water discharging member is installed.

A sealing protrusion 7611 may protrude upward from the window-bottom-surface supporting surface 761. The sealing protrusion 7611 may have a square shape that is smaller than the window-lateral surface-lower-portion supporting surface 762 and that is larger than the upper end portion of the funnel part 753 (ref. FIG. 7). The sealing protrusion 7611 may be provided near the nozzle 75 in the window accommodating part 76, 78. Thus, water in the nozzle 75 may be prevented from leaking into the light-source bracket 77 from the inlet of the path where water enters the elbow 74. A square edge of the sealing protrusion 7611 may be rounded so as to prevent a below-described sealing member 87 from being torn.

The window-lateral-surface-lower-portion supporting surface 762 may include a lower arranging member (or tab guide) 763 on the outer surface thereof. The tab guide 763 may be provided in an area opposite to the area where the water-supplying-hose barb 72 is placed. Accordingly, the water discharging member 70 may be placed in the front-rear direction in a compact manner. The tab guide 763 may be engaged with a below-described upper arranging member (or tab) 783 of the light-source bracket 77 so as to determine a direction in which the nozzle 71 and the light-source bracket 77 are assembled.

A lower engaging protrusion (or lip) 764 may protrude upward from the window-lateral-surface-lower-portion supporting surface 762. The lower engaging protrusion 764 may have a shape that is complementary to that of a below-described upper engaging protrusion 784 and may be engaged with the upper engaging protrusion.

The elbow 74 may connect with one lateral surface and the front surface of the nozzle pipe 75 while encircling the same. Referring to FIG. 7, the center (O) of the nozzle pipe 75 may be arranged slightly backward with respect to the center of the window pocket 76. In other words, the elbow 74 may be provided slightly forward with respect to the center of the window pocket 76 while the nozzle pipe 75 may be disposed slight backward with respect the center of the window pocket 76. Accordingly, a nozzle member may be placed in the front-rear direction in a compact manner.

A light source 80 may be installed in the light-source bracket 77. The light source 80 may include a substrate 81 that has the shape of a long rectangular plate, a UV LED 83 that is mounted onto the lower surface of one side of the substrate 81, and a connector 82 that is mounted onto the upper surface of the other side of the substrate 81. A power cable that supplies electric power to the UV LED 83 may connect to the connector 82.

The UV LED 83 may have the shape of a chip. A first lens may be integrally provided in the UV LED 83. The first lens may properly adjust radiation angles of ultraviolet light that is radiated from the UV LED 83.

A wavelength of 253 nm of ultraviolet light may have excellent sterilizing power. However, implementations may be focused on sterilizing bacteria that can breed in a space where water flows. Accordingly, a peak wavelength of ultraviolet light having excellent sterilizing power may be radiated to bacteria.

Ultraviolet light radiated from the UV LED 83 may have a peak wavelength of 265 nm to 275 nm and may be deep ultraviolet (UVC) light that have a peak wavelength of 270 nm. DNA of *E. coli* O157:H7 (ATCC 43894), *B. subtilis* spore (ATCC 6633), and B. MS2 phage (ATCC 15597-B1) that may be bacteria inhabiting in a damp environment have a sensitivity to ultraviolet light having a wavelength of 270 nm. Additionally, when ultraviolet light is emitted having a wavelength near 270 nm, electric energy may be efficiently converted into deep ultraviolet light (UVC) in the UV LED. Thus, when ultraviolet light radiated from the UV LED has a peak wavelength of 270 nm, bacteria may be effectively sterilized. Additionally, unlike usual ultraviolet lamps, the UV LED may have a high degree of intensity of ultraviolet radiation near a peak wavelength. Thus, with the UV LED 83 that radiates ultraviolet light having a peak wavelength of 270 nm, bacteria may be more efficiently sterilized.

The substrate 81 may be fixed to a substrate fixing part (or substrate base) 771 of the light-source bracket 77. The substrate base 771 may include a space having a rectangular shape that corresponds to the shape of the substrate 81. The substrate base 771 may extend horizontally with respect to the central axis (O) of the nozzle pipe 75 in a direction opposite to the direction where the water-supplying-part connecting pipe 72 is provided. In other words, the substrate base 771 and the water hose barb 72 may oppositely extend with respect to the nozzle pipe 75.

The substrate base 771 may extend from the nozzle pipe 75 in any one of the left and right directions while the water hose barb 72 may extend in the other direction. Accordingly, the light source 80 may be integrally installed in the water discharging member 70 while the length of the water discharging member in the front-rear direction is maintained in a compact manner.

The substrate base 771 may include a space that has the shape of a groove and that may accommodate the substrate, and a fixing protrusion 772 so as to encircle at least a part of the space. The fixing protrusion 772 may support a lateral surface of the substrate 81.

The fixing protrusion 772 may further include, on an inner surface thereof, a hook shape that guides the substrate 81 such that the substrate is inserted into the substrate base 771 and that prevents the substrate 81 from escaping from the substrate base 771.

A light passing hole 773 may be provided in a portion of the light-source bracket 77, which faces the UV LED. The light passing hole 773 may be provided on the floor surface of the substrate base 771. The UV LED 83 may be accommodated in the light passing hole 773 and may face downward in the state where the substrate 81 is installed in the substrate base 771. The window 85 and the inner space of the nozzle pipe 75 may be seen from the UV LED 83 through the light passing hole 773.

A diameter of the funnel 753 of the nozzle pipe 75 may become larger toward the upper portion thereof, i.e., toward the UV LED. Accordingly, the nozzle pipe 75 may receive a large amount of ultraviolet radiation in the inner space thereof.

The light passing hole 773 may include a seal pocket or upper groove 78 (second-portion accommodating part) around the perimeter thereof, which may extend downward from the bottom surface of the substrate base 771. The seal pocket 78 and the window pocket or lower groove 76 may constitute a window accommodating part. In other words, the window accommodating part may be divided into the first-portion accommodating part 76 that connects with the nozzle pipe 75, and the second-portion accommodating part 78 that connects with the light-source bracket 77.

The seal bracket 78 may include a window-upper-surface supporting surface 781 (second-surface supporting surface) that may form a peripheral portion of the light passing hole 773 on the bottom surface of the substrate base 771, and a window-lateral-surface-upper-portion supporting surface 782 (lateral-surface-second-portion supporting surface) that may extend downward from the edge of the second-window-upper-surface supporting surface 781 on the bottom surface of the substrate base 771.

The window-upper-surface supporting surface 781 (second-surface supporting surface) may support a second surface 852 (upper surface) of the window member 85. The window-lateral-surface-upper-portion supporting surface 782 (lateral-surface-second-portion supporting surface) may support the upper portion of a lateral surface 853 of the window member 85.

The window-lateral-surface-upper-portion supporting surface 782 may include an upper arranging member (or tab) 783 on the outer surface thereof. The upper arranging member 783 may connect to the window-lateral-surface-upper-portion supporting surface 782 and/or the bottom surface of the substrate base 771 that is adjacent to the window-lateral-surface-upper-portion supporting surface. The upper arranging member 783 may be provided in an area opposite to the area where the water-supplying hose barb 72 is placed and in a position corresponding to the lower arranging member 763.

According to embodiments, the upper arranging member 783 may have the shape of a protrusion that extends downward while the lower arranging member 763 may have the shape of a groove that accommodates the protrusion. In other words, the upper arranging member 783 and the lower arranging member 763 may have a complementary shape.

The upper arranging member 783 and the lower arranging member 763 may determine a direction where the nozzle 71 and the light-source bracket 77 are assembled. In other words, when the window pocket 76 and the seal pocket 78 are coupled such that the upper arranging member 783 and the lower arranging member 763 are engaged with each other, the water-supplying hose barb 72 and the light-source bracket 77 may extend and be arranged in directions opposite to each other with respect to the nozzle pipe 75.

Additionally, to prevent the nozzle part and the light-source installing part from being assembled incorrectly, when the window pocket 76 and the seal pocket 78 are arranged so as to face each other and approach each other in the state where the upper arranging member 783 and the lower arranging member 763 do not meet each other, at least one of the upper arranging member 783 and the lower arranging member 763 may interfere with the other such that surfaces of the window pocket 76 and the seal pocket 78 are prevented from being contacted.

The window accommodating parts 76, 78 may have the shape of a square. Accordingly, the window accommodating parts may be engaged with each other largely in four directions. The window pocket 76 and the seal pocket 78 may be exactly engaged with each other only when the window accommodating parts are engaged in one correct direction.

The window pocket 76 may be integrally formed with the nozzle 71 while the seal pocket 78 may be integrally formed with the light-source bracket 77. Divided portions between the window pocket 76 and the seal pocket 78 may be bonded with each other.

The window-lateral-surface-upper-portion supporting surface 782 may include an upper engaging protrusion (or lip) 784 (second engaging protrusion) that protrudes downward from the window-lateral-surface-upper-portion supporting surface. Any one of the upper engaging protrusion 784 and lower engaging protrusion 764 may encircle the other. According to embodiments, the upper engaging protrusion 784 may encircle the lower engaging protrusion 764. Conversely, the lower engaging protrusion 764 may encircle the upper engaging protrusion 784.

The surface of the lower end of the upper engaging protrusion 784 may contact the window-lateral-surface-lower-portion supporting surface 762 (ref. w1). The surface of the upper end of the lower engaging protrusion 764 may contact the window-lateral-surface-upper-portion supporting surface 782 (ref. w2). The lateral surfaces of the upper engaging protrusion 784 and the lower engaging protrusion 764 may contact each other (ref. w3).

The water discharging member may be bonded with at least one of a surface (w2) where the surface of the distal end of the first engaging protrusion 764 and the seal pocket 78 face each other, a surface (w1) where the surface of the distal end of the second engaging protrusion 784 and the window pocket 76 face each other, and a surface (w3) where the lateral surface of the first engaging protrusion 764 and the lateral surface of the second engaging protrusion 784 face each other. The bonded surface may be ultrasonic-welded.

An inclined weld surface 785 may be provided on any one of the later surfaces of the first engaging protrusion 764 and the second engaging protrusion 784 that face each other. The inclined weld surface 785 may be welded in the step of ultrasonic welding. In embodiments, the inclined weld surface 785 may be provided on the lateral surface of the second engaging protrusion 784. While the inclined weld surface temporarily melts, the inclined weld surface may spread into the gaps between the surfaces (w1, w2, and w3), and the surfaces (w1, w2, and w3) may be firmly welded.

A window or transparent plate 85 may be accommodated in the window accommodating part 76, 78. The window 85 may have a size that is smaller than that of a space defined by the window accommodating part 76, 78. That is, the space defined by the window accommodating part 76, 78 may have a shape that corresponds to that of the window member and may be larger than that of the window member.

The window accommodating part 76, 78 may include a supporting surface 761, 762, 781, 782 that face the window member accommodated in the window accommodating part. A seal 87 may be interposed between the window 85 and the supporting surface 761, 762, 781, 782 of the window accommodating part 76, 78. The seal 87 may have a thickness that is greater than the gap between the supporting surface 761, 762, 781, 782 and the window 85. Accordingly, the seal 87 may be compressed between the supporting surface 761, 762, 781, 782 and the window 85.

Deep ultraviolet (UVC) light may have low transmittance, and high reflectivity and high scattering rates because deep ultraviolet light has a wavelength shorter than that of visible light and energy higher than that of visible light. Accordingly, when the window 85 is based on a usual transparent plastic material, transmittance of ultraviolet light is less than 50%. Energy of ultraviolet light that is not transmitted may degrade the material of the window 85. Thus, when the window 85 is based on a material that has low transmittance of ultraviolet light, the window 85 may be degraded and transmittance of ultraviolet light may be lowered.

A material that has high transmittance of deep ultraviolet light may be used for the window 85 such that ultraviolet rays of the light source 80 may reach a space required to be sterilized. Accordingly, the window 85 may include quartz. In addition to quartz, polymethyl methacrylate (PMMA) that has high monomer yield may be used for the window 85. The monomer yield may be 80% or more such that ultraviolet rays are transmitted to the extent that the ultraviolet rays may not degrade the window 85. Additionally, when fluoro resins are used for the window 85, deep ultraviolet light may not degrade the window member. For instance, a "TEFLON"-based fluoro resin of "DUPONT" may be used as a fluoro resin.

The window 85 may have the shape of a plate and have a predetermined thickness. In embodiments, the plate may have the shape of a square that correspond to the shape of the window accommodating part 76, 78. The window 85 may have a circular shape, and the like. However, the shape of the window member may not be restricted.

The window 85 may include a first surface 851 (lower surface), a second surface 852 (upper surface) that is a surface opposite to the first surface 851 and a lateral surface 853 that connects the first surface 851 and the second surface 852. The first surface 851 may face the nozzle pipe 75, and the second surface 852 may face the light source 80. The first surface 851 and the second surface 852 may be mirror-surface-treated so as to minimize reflection of ultraviolet light. Additionally, when total reflection happens on the first surface (lower surface), ultraviolet light may not reach the inside of the nozzle pipe 75. To prevent this, a radiation angle of the UV LED 83 may not be wide. The radiation angle may be a maximum of 60 degrees.

Any one of the first surface and the second surface of the window 85 may be sand-blasted such that the ultraviolet light generated by the light source may not concentrate on a specific area. Total reflection may be likely to happen on the first surface. Accordingly, the second surface may be sand-blasted. Thus, a sand-blasted surface may be a surface that has fine curves and that is rough, and through sand blasting, ultraviolet light that is a point light source radiated by the UV LED may be converted into a surface light source.

The light-source bracket 77 and the nozzle 71 may face each other with the window 85 between the light-source bracket 77 and the nozzle 71. Additionally, the substrate base 771 of the light-source bracket 77 may extend in a direction opposite to the water-supplying hose barb 72 with respect to the window 85.

The light source 80 may directly radiate ultraviolet light into at least a portion (first portion) of the inner wall surface of the nozzle pipe 75. Ultraviolet light reflected from the first portion may be radiated onto the inner wall surface (second portion) of the nozzle pipe 75 into which ultraviolet light is not directly radiated from the light source 80. The inner wall surface of the nozzle pipe 75 may be treated to successfully reflect ultraviolet light such that ultraviolet light is evenly radiated onto the inner wall surface that has various shapes 751, 74.

Further, the inner wall surface of the water-supplying hose barb 72 may also be treated to successfully reflect ultraviolet light. To this end, the inner wall of the nozzle 71 may be coated with aluminum. Further, the inner wall may be surface-treated to prevent aluminum from dissolving into water.

The seal 87 may include a lateral-surface encircling part 873 that contacts and encircles the lateral surface 853 of the window 85, a first-surface edge part 871 that is compressed and interposed between the first surface 851 of the window member and the window-bottom-surface supporting surface 761 and that connects to the lower end portion of the lateral-surface encircling part 873, and a second-surface edge part 872 that is compressed and interposed between the second surface 852 of the window member and the window-upper-surface supporting surface 781 of the window member and that connects to the upper end portion of the lateral-surface encircling part 873. The first-surface edge part 871 may be engaged with the sealing protrusion 7611 and may prevent water in the nozzle pipe 75 from flowing into the light-source bracket 77.

The lateral-surface encircling part 873 may touch and contact the window-lateral-surface-lower-portion supporting surface 762 and the window-lateral-surface-upper-portion supporting surface 782. Accordingly, the lateral-surface encircling part 873 may cover a boundary surface between the window-lateral-surface-lower-portion supporting surface 762 and the window-lateral-surface-upper-portion supporting surface 782.

When the window pocket 76 and the seal pocket 78 accommodate the window 85 and the seal 87 and are compressed with respect to each other, the seal 87 may seal the water discharging member while being compressed. In this state, when a portion where the window-lateral-surface-lower-portion supporting surface 762 and the window-lateral-surface-upper-portion supporting surface 782 are engaged is ultrasonic-welded, the portion may be firmly welded. Further, a boundary surface between the window-lateral-surface-lower-portion supporting surface 762 and the window-lateral-surface-upper-portion supporting surface 782 that melts in the process of ultrasonic welding may be more firmly integrated into the lateral-surface encircling part 873 of the seal 87.

According to the water discharging member 70 of implementations, the seal 87 may be compressed by a force that contacts the nozzle 71 and the light-source bracket 77 to couple the nozzle 71 and the light-source bracket 77, and a boundary surface between the window-lateral-surface-lower-portion supporting surface 762 and the window-lateral-surface-upper-portion supporting surface 782, which melts in the process of ultrasonic welding, may be integrated with the seal 87. Thus, the water discharging member may be easily manufactured and may be definitely sealed.

The nozzle pipe 75 may include a key 752 that radially protrudes outward from the outer circumference thereof. The key 752 may be provided in the lower end portion of the small diameter part 754 of the nozzle pipe 75. The key 752 may fix the water discharging member 70 to the dispenser housing 50.

With reference to FIG. 2 and FIGS. 8 to 10, a structure where a water discharging member is installed will be described. The water discharging member 70 may be installed in a nozzle supporting part (or nozzle support) 551 of a dispenser housing 50.

The nozzle support 551 may include a nozzle coupling hole 56 that has the shape of a hole that is penetrated upward and downward. The nozzle coupling hole 56 may have the shape of a circular hole and may have an inner diameter that corresponds to outer diameter of the small diameter part 754 of the water discharging member 70. Accordingly, when the small diameter part 754 of the nozzle pipe 75 is inserted into the nozzle supporting part 551, the water discharging member 70 may only move upward and downward and rotate around the axis (O).

A key groove 57 that extends upward and downward may be provided in the nozzle coupling hole 56. The key groove 57 may be a passage where the key 752 is accommodated and may move while the small diameter part 754 of the nozzle pipe 75 is inserted into the nozzle support 551. The water discharging member 70 may not rotate when the key is accommodated in the key groove.

A coupling space 59 that extends by a predetermined angle in a direction of the perimeter of the circumference may be provided in the lower end portion of the key groove 57. When the water discharging member 70 rotates by the predetermined angle when the small diameter part 754 of the nozzle pipe is inserted into the nozzle coupling hole 56, the key 752 may move from the key groove 57 to the coupling space 59. In other words, an angle at which the water discharging member 70 may rotate may be limited to a range of the extension of the coupling space 59.

The lateral surface of the key 752 that is moved to the coupling space 59 may contact the lateral wall of the coupling space 59 while the upper surface of the key contacts a supporting surface 58 that is provided in the lower portion of the nozzle support 551. In other words, the rotation and upward movement of the water discharging member 70 may be limited in the state where the key 752 is coupled into the coupling space 59.

The downward movement of the water discharging member 70 may be limited by interference of the outer surface of the funnel part 753 of the water discharging member 70 and the nozzle support 551. Specifically, in the nozzle support 551, the funnel accommodating hole 561 that has an inner diameter greater than that of the nozzle coupling hole 56 may be provided in the upper portion of the nozzle coupling hole 56. The funnel accommodating hole 561 may be a space in which the funnel part 753 may be accommodated.

An inclined surface 565 that corresponds to the outer surface of the funnel part may be provided in the upper portion of the funnel accommodating hole 561. The inclined surface 565 may have the shape of a hole the diameter of which becomes larger toward the upper portion thereof. The inclined surface 565 may guide the water discharging member 70 such that the water discharging member is fitted into the nozzle coupling hole 56 in the step where the water discharging member 70 is initially inserted. The inclined surface 565 may interfere with the outer circumferential surface of the funnel part 753 when the water discharging member 70 is inserted and the key 752 reaches a height the same as that of the coupling space 59 so as to prevent the water discharging member 70 from moving further downward.

The water discharging member 70 may be inserted to a depth defined by the nozzle support 551 and then rotated by the predetermined angle. Thus, the water discharging member 70 may be installed.

Referring to FIG. 2, the water discharging member 70 may be provided at the front of the discharge funnel 54 when the water discharging member 70 is installed, As described above, the upper space of the nozzle support 551 may be narrow in the front-rear direction while slightly spacious in the left-right direction.

The light-source bracket 77 of the water discharging member 70 may extend to the left with respect to the nozzle pipe 75, the water-supplying hose barb 72 may extend to the right with respect to the nozzle pipe 75, and the water discharging member may be installed in the space in a compact manner. Further, the water-supplying hose barb 72 may extend backward and upward. Accordingly, the water-supplying-part connecting pipe may avoid the discharge funnel 54.

In a refrigerator with a dispenser that may sterilize bacterial using ultraviolet light, bacteria may be periodically sterilized with ultraviolet light. For instance, the light source 80 may be turned on for five minutes per hour. That is, the light source may be turned on for five minutes and turned off for 55 minutes.

The ultraviolet sterilization may also be performed with the user's instruction. Even in this case, the ultraviolet sterilization may be performed for about five minutes.

On condition that ultraviolet light has the same peak wavelength, efficiency of ultraviolet sterilization may be proportional to intensity of ultraviolet light and a period of time for which ultraviolet light is radiated. It may take five minutes to sterilize about 99.99 or more % of the above-described bacterial using the UV LED of implementations.

In a water discharging member according to embodiments, a structure where an ultraviolet light source is installed, and a structure where water is supplied to a nozzle part of the water discharging member extend may be provided in directions opposite to each other with respect to the nozzle part, thereby making it possible to allow the water discharging member to have a compact structure while a ultraviolet sterilization structure is applied to the water discharging member. The water discharging member according to embodiments may radiate ultraviolet light of a peak wavelength with high sterilizing power, thereby enhancing efficiency of sterilization.

The water discharging member according to embodiments may radiate deep ultraviolet (UVC) light through a window member that transmits deep ultraviolet light effectively, thereby enhancing efficiency of sterilization. The water discharging member according to embodiments may increase reflectivity of ultraviolet light of a surface to be sterilized and allow ultraviolet light to reach the surface to be sterilized as a whole, thereby enhancing efficiency of sterilization.

The water discharging member according to embodiments may have a structure where a direction in which two parts that accommodate a window member and a sealing member are coupled is matched with a direction where the sealing member is compressed, such that the two parts are welded in the state where the sealing part is compressed by the force that couples the two parts, thereby making it possible to easily manufacture the water discharging member and make the water discharging member definitely watertight. The water discharging member according to embodiments may include a key, and a dispenser housing in which the water discharging member is installed may include a key groove that is engaged with and fixed to the key, thereby making it possible to easily assemble the water discharging member and definitely fix the same.

A water discharging member according to an embodiment may include a nozzle pipe 75 one end of which introduces water, the other end of which discharges water and that has an inner space where water flows; a light source 80 that radiates ultraviolet light from one end of the nozzle pipe 75 to the inner space of the nozzle pipe 75; and a window member 85 that is disposed between one end of the nozzle pipe 75 and the light source, that divides the inner space of the nozzle pipe and an area where the light source is disposed and that transmits ultraviolet light radiated from the light source 80 to the nozzle pipe 75. At least a part of an inner wall surface of the nozzle pipe 75 may directly face the light source and receive ultraviolet light. The other part of the inner wall surface of the nozzle pipe 75 may receive ultraviolet light that is reflected from at least a part of the inner wall surface of the nozzle pipe 75, which directly faces the light source and receives the light.

The window member may be accommodated in a window accommodating part 76, 78. A space defined by the window accommodating part 76, 78 may have a shape that corresponds to that of the window member and may be larger than that of the window member. The window accommodating part 76, 78 may be provided with a supporting surface 761, 762, 781, 782 that faces the window member accommodated in the window accommodating part.

A water-supplying-part connecting pipe 72 may connect to one end of the nozzle pipe 75. The water-supplying-part connecting pipe 72 may connect to the nozzle pipe close to the window accommodating part. The water-supplying-part connecting pipe 72 may connect with a lateral surface of the nozzle pipe 75.

At least a part of the inner wall surface of the water-supplying-part connecting pipe 72 may directly face the light source and receive ultraviolet light. The other part of the inner wall surface of the water-supplying-part connecting pipe 72 may receive ultraviolet light that is reflected from at least a part of the inner wall surface of the water-supplying-part connecting pipe 72, which directly faces the light source.

The inner wall surfaces of the nozzle pipe 75 and/or the water-supplying-part connecting pipe 72 may be surface-treated so as to successfully reflect ultraviolet light. The inner wall surfaces may be coated with aluminum.

The light source 80 may be installed in a light-source installing part 77. The light-source installing part 77 may be disposed opposite the water-supplying-part connecting pipe 72 with the window accommodating part between the light-source installing part and the water-supplying-part connecting pipe. The light-source installing part 77 may extend in a direction opposite to the direction where the water-supplying-part connecting pipe 72 extends with respect to the nozzle pipe 75.

The light source 80 may include a substrate 81, a UV LED 83 (ultraviolet light-emitting diode) that is installed at one end of the substrate 81, and a connector 82 that is installed at the other end of the substrate 81. The UV LED may be installed on a first surface of the substrate 81, and the connector 82 may be installed on a second surface opposite to the first surface of the substrate 81.

The light-source installing part 77 may include a substrate fixing part 771 in which the substrate 81 is accommodated, and a fixing protrusion 772 that prevents the substrate 81 accommodated in the substrate fixing part 771 from escaping. The fixing protrusion 772 may support a lateral surface of the substrate 81.

A light passing hole 773 may be provided in a portion of the light-source installing part 77, which faces the UV LED. The window member 85 may be seen through the light passing hole 773 from the UV LED 83.

The window member 85 may include a first surface 851 that faces the nozzle pipe 75; a second surface 852 that faces the light source 80; and a lateral surface 853 that connects the first surface 851 and the second surface 852. The window member 85 may have the shape of a plate that has a predetermined thickness. The plate may have a square shape or a circular shape.

Quartz, PMMA that has monomer yield of 80% or more, or a "TEFLON"-based fluoro resin of "DUPONT", and the like may be used for the window member 85. The window accommodating part may include a first-portion accommodating part 76 and a second-portion accommodating part 78 that are divided in a portion that faces the lateral surface of the window member.

The window accommodating part may be divided into a first-portion accommodating part 76 that connects with the nozzle pipe 75 and a second-portion accommodating part 78 that connects with the light-source installing part 77. The first-portion accommodating part 76 may be integrally formed with the nozzle part 71. The second-portion accommodating part 78 may be integrally formed with the light-source installing part 77.

Portions where the first-portion accommodating part 76 and the second-portion accommodating part 78 are divided may be bonded to each other. The first-portion accommodating part 76 and the second-portion accommodating part 78 may be ultrasonic-welded and bonded to each other.

The first-portion accommodating part 76 may include a first engaging protrusion 764 that extends toward the second-portion accommodating part 78, while the second-portion accommodating part 78 may include a second engaging protrusion 784 which extends toward the first-portion accommodating part 76 and the lateral surface of which faces a lateral surface of the first engaging protrusion 764. The first-portion accommodating part 76 and the second-portion accommodating part 78 may be bonded with least one of a surface (w2) where the surface of the distal end of the first engaging protrusion 764 faces the second-portion accommodating part 78, a surface (w1) where the surface of the distal end of the second engaging protrusion 784 faces the first-portion accommodating part 76, and a surface (w3) where a lateral surface of the first engaging protrusion 764 faces a lateral surface of the second engaging protrusion 784.

An inclined weld surface 785 may be provided on any one of the lateral surfaces of the first engaging protrusion 764 and the second engaging protrusion 784 that face each other and may be welded in the step of ultrasonic welding. An upper arranging member 783 may be provided on one side of the first-portion accommodating part 76, and a lower arranging member 763 that has a shape complementary to the upper arranging member 783 may be provided on one side of the second-portion accommodating part 78. When the first-portion accommodating part 76 and the second-portion accommodating part 78 are coupled such that the upper arranging member 783 and the lower arranging member 763 are engaged with each other, the water-supplying-part connecting pipe 72 and the light-source installing part 77 may be extend and arranged in directions opposite to each other with respect to the nozzle pipe 75.

When the first-portion accommodating part 76 and the second-portion accommodating part 78 are arranged so as to face each other and approach each other in the state where the upper arranging member 783 and the lower arranging member 763 do not meet each other, at least one of the upper arranging member 783 and the lower arranging member 763 may interfere with the other, and surfaces of the first-portion accommodating part 76 and the second-portion accommodating part 78 may not be contacted. Accordingly, the first-portion accommodating part 76 and the second-portion accommodating part 78 may be prevented from being misaligned before the first-portion accommodating part 76 and the second-portion accommodating part 78 are bonded.

A sealing member 87 may be accommodated in the window accommodating part. The sealing member 87 may be interposed between the window member and the supporting surface. The sealing member 87 may include a lateral-surface encircling part 873 that is disposed between the lateral surface 853 of the window member and a divided portion of the window accommodating member. Accordingly, the divided portion may be definitely sealed.

The lateral-surface encircling part 873 may face and contact a bonded portion of the first-portion accommodating part 76 and the second-portion accommodating part 78. The first-portion accommodating part 76 may include a first-surface supporting surface 761 that faces the edge of a first surface, and the sealing member 87 may include a first-surface edge part 871 that is disposed between the first-surface supporting surface 761 and the first surface 851.

A sealing protrusion 7611 that has the shape of a closed loop and that pressurizes the sealing member 87 may protrude from the first-surface supporting surface 761. Accordingly, the first surface that is placed near a space where water flows may be sealed, thereby making it possible to increase water tightness.

The second-portion accommodating part 78 may include a second-surface supporting surface 781 that faces the edge of a second surface, and the sealing member 87 may include a second-surface edge part 872 that is disposed between the second-surface supporting surface 781 and the second surface 852. The first-surface edge part 871 and the lateral-surface encircling part 873 may connect with each other. The second-surface edge part 872 and the lateral-surface encircling part 873 may connect with each other.

The first-surface edge part 871 may connect to one end of the lateral-surface encircling part 873, and the second-surface edge part 872 may connect to the other end of the lateral-surface encircling part. The first-surface edge part 871 and the second-surface edge part 872 may face each other with the lateral-surface encircling part 873 between the first-surface edge part and the second-surface edge part.

A central axis (O) of the nozzle pipe 75 in the lengthwise direction thereof, and a central axis (P) of the water-supplying-part connecting pipe 72 in the lengthwise direction thereof may be disposed so as not to meet each other and not to be parallel.

The water-supplying-part connecting pipe 72 may communicate with the nozzle pipe 75 while contacting the same such that the central axis (P) of the water-supplying-part connecting pipe 72 in the lengthwise direction thereof escapes from the inner area of the nozzle pipe 75. Accordingly, water that is supplied to the nozzle pipe 75 through the water-supplying-part connecting pipe 72 may cause a swirl while flowing along the perimeter of the inner wall of the nozzle pipe 75. The swirl may stabilize the flow of water that is discharged from a water discharging member and prevent water from remaining in the nozzle pipe 75.

The water-supplying-part connecting pipe 72 may extend inclinedly with respect to a surface (perpendicular plane) perpendicular to the central axis (O) of the nozzle pipe 75 in the lengthwise direction thereof. Thus, water may not stagnate in the water-supplying-part connecting pipe 72 and may not be left in the nozzle pipe 75 because the water that is supplied through the water-supplying-part connecting pipe 72 may be supplied to the nozzle pipe 75 while having the kinetic energy of a downward motion.

A funnel part 753 that communicates with the water-supplying-part connecting pipe 72 may be provided at one end of the nozzle pipe 75. The funnel part 753 may have a shape the inner diameter of which becomes narrower from one end of the nozzle pipe 75 to the other end of the nozzle pipe.

The funnel part 753 may have a surface large enough to receive ultraviolet light that is radiated from the light source because one end of the funnel part may have a large diameter.

A small diameter part 754 that has the shape of a cylinder and that connects with the funnel part 753 may be provided at the other end of the nozzle pipe 75. The small diameter part 754 may connect with the funnel part 753, and the inner diameter of the small diameter part 754 may correspond to the inner diameter of a portion of the funnel part 753 that connects with the small diameter part 754.

A laminar-flow protrusion 751 that protrudes inward to the center of the small diameter part 754 and that extends in the lengthwise direction of the small diameter part 754 may be provided in a portion of the small diameter part 754, which is adjacent to the funnel part 753. The water supplied from the water-supplying-part connecting pipe 72 may move downward while hovering in the funnel part 753, may be collected in the small diameter part 754 and may be turned into laminar flow by the laminar-flow protrusion 751. Thus, flow of water that is supplied to the user through the other end of the nozzle pipe 75 may be stabilized.

The light source 80 may radiate ultraviolet light that has a peak wavelength within a range of 265 nm to 275 nm. DNA or RNA of bacteria that inhabit in a damp environment such as *E. coli* O157:H7 (ATCC 43894), *B. subtilis* spore (ATCC 6633), and B. MS2 phage (ATCC 15597-B1) reacts sensitively to a wavelength of 270 nm. Accordingly, when a peak wavelength of ultraviolet light radiated from the light source 80 is near 270 nm, efficiency of sterilization may significantly improve.

In a refrigerator according to an implementation, a dispenser housing 50 to which the water discharging member 70 is coupled may be installed in a door 20. The dispenser housing 50 may include a nozzle coupling hole 56 that extends vertically and that is engaged with the outer circumferential surface of the nozzle pipe 75 of the water discharging member 70. Thus, the water discharging member 70 may be installed in the dispenser housing 50 while the position of the water discharging member is exactly regulated.

The nozzle pipe 75 may be provided with a key 752 that radially protrudes outward on the outer circumferential surface of the other end thereof. A key groove 57 that extends in the lengthwise direction of the nozzle coupling hole 56 may be provided in an inner surface of the nozzle coupling hole 56 such that the key 752 passes through.

A coupling space 59 that extends in the circumferential direction and that communicates with the key groove 57 may be provided in the lower end portion of the nozzle coupling hole 56, and a supporting surface 58 that supports the upper surface of the key 752 may be provided in the upper end portion of the coupling space 59. Accordingly, the nozzle pipe 75 may be inserted into the nozzle coupling hole 56 in the lengthwise direction of the nozzle coupling hole 56.

When the nozzle pipe 75 rotates after being inserted into the nozzle coupling hole, the key 752 may move circumferentially into the coupling space 59. Then the key 752 may be supported by the supporting surface 58 and may prevent the nozzle pipe 75 from escaping. The funnel part 753 that has a shape the outer diameter of which becomes narrower from one end of the nozzle pipe 75 to the other end of the nozzle pipe may be provided at one end of the nozzle pipe 75, and the small diameter part 754 that has the shape of a cylinder and that connects with the funnel part 753 may be provided in the other end of the nozzle pipe 75.

The key 752 may be provided on the outer circumferential surface of the small diameter part 754, the nozzle coupling hole 56 may be engaged with the outer circumferential surface of the small diameter part 754, a depth to which the nozzle pipe 75 is inserted into the nozzle coupling hole 56 may be regulated by interference of the funnel part 753 and the dispenser housing 50. A portion of the dispenser housing 50, which interferes with the funnel part 753 has a space greater than that of the small diameter part 754. Accordingly, the portion of the dispenser housing 50, which interferes with the funnel part 753, may guide the water discharging member such that the water discharging member is assembled.

Effects of a water discharging member according to embodiments and a refrigerator that is provided with a dispenser having the water discharging member are described as follows. The water discharging member according to embodiments may have a compact structure and, accordingly, may be easily installed in a narrow door of the refrigerator and readily maintained and repaired.

The inner wall surface of the water discharging member according to embodiments, which contacts water, may be definitely sterilized and, accordingly, the water discharging member may not need to be replaced with a new one due to bacterial growth.

The water discharging member according to embodiments may have a simple structure and may be easily manufactured although a water tight structure is applied to the water discharging member. The water discharging member according to embodiments may be definitely watertightened although the water discharging member may have a simple structure and may be easily manufactured.

The water discharging member according to embodiments may take up little space although ultraviolet sterilization is applied to the water discharging member, and, accordingly, volume of the refrigerator may increase. The inner wall surface of the water discharging member according to embodiments may be definitely sterilized while the water discharging member has a compact structure.

Embodiments disclosed herein may be implemented as a refrigerator comprising a cabinet having a storage space, and a door configured to open or close the storage space, the door having a dispenser. The dispenser may include a dispenser housing, a nozzle coupling hole formed in a lower portion of the dispenser housing, wherein a key groove is formed in the nozzle coupling hole, a nozzle pipe having a key, the nozzle pipe being configured to be inserted in the nozzle coupling hole and the key groove being configured to be inserted in the key groove to couple the nozzle pipe to the dispenser housing, a liquid-supplying hose barb extending, via an elbow, from the nozzle pipe at an inclination with respect to the nozzle pipe, and a hose coupled to the liquid-supplying hose barb. The liquid-supplying hose barb may be inclined with respect to a plane perpendicular to an axial direction of the nozzle pipe.

The nozzle pipe may include a first end which receives liquid, a second end through which the liquid is discharged, a funnel space provided at the first end of the nozzle pipe that communicates with the liquid-supplying hose barb, and a cylindrical space that connects with the funnel space and provided at the second end of the nozzle pipe. The funnel space may have an inner diameter which becomes narrower in a direction from the first end of the nozzle pipe to the second end of the nozzle pipe.

At least one laminar flow protrusion may be provided in the cylindrical space and protruded inward toward a center of the cylindrical space. The laminar flow protrusion may extend in an axial direction of the cylindrical space.

The key may be provided on an outer circumferential surface of a portion of the nozzle pipe that defines the cylindrical space. The nozzle coupling hole may be engaged with the outer circumferential surface of the portion of the nozzle pipe.

An outer diameter of a funnel portion of the nozzle pipe defining the funnel space may narrow in a direction from the first end to the second end of the nozzle pipe. A depth to which the nozzle pipe inserted into the nozzle coupling hole may be based on a contact between the funnel portion and the dispenser housing.

The key groove may extend in a longitudinal direction of the nozzle coupling hole. The nozzle coupling hole may further comprise a coupling space provided at a bottom of the nozzle coupling hole and communicating with a bottom of the key groove, and a supporting surface defining a top of the coupling space to support an upper surface of the key.

The liquid-supplying hose barb may be positioned such that a central axis of the nozzle pipe and a central axis of the liquid-supplying hose barb do not intersect with each other.

Embodiments disclosed herein may be implemented as a liquid dispenser comprising a nozzle pipe including a first section having a first passage and a second section having a second passage communicating with the first passage, wherein the second passage has a cylindrical shape with a diameter smaller than a diameter of the first passage, a window pocket provided above the first section of the nozzle pipe, a light source provided above the window pocket and configured to emit ultraviolet light into the first passage, a window provided in the window pocket to be between the first passage and the light source, an elbow branched from the first section of the nozzle pipe at an inclination with respect to the nozzle pipe, a liquid-supplying hose barb extending from the elbow at the inclination, and a hose coupled to the liquid-supplying house barb. A center axis of the first section of the nozzle pipe may not intersect with a center axis of the liquid-supplying hose barb such that liquid discharged from the elbow and entering the liquid-supplying hose barb may flow along the first section of the nozzle pipe in a swirling flow.

An inner space of the elbow may communicate with the nozzle pipe such that a central axis of the elbow passes through an inner area of the nozzle pipe. A central axis of the liquid-supplying hose barb may be positioned to pass outside of an inner area of the nozzle pipe.

The liquid-supplying hose barb may be inclined with respect to a plane which may be perpendicular to a central axis of the nozzle pipe. The elbow may be configured to connect with the nozzle pipe to contact an outer surface of the nozzle pipe.

The nozzle pipe may include a first end which receives liquid and a second end through which the liquid may be discharged, and the first passage may have an inner diameter which becomes narrower in a direction from the first end of the nozzle pipe toward the second end of the nozzle pipe.

A laminar flow protrusion may be provided in the second passage and protrude inward from an inner surface of the second section toward a center of the second passage. The laminar flow protrusion may extend in an axial direction of the second passage.

An inner surface of the liquid-supplying hose barb and an inner surface of the nozzle pipe may be coated with aluminum. A seal may be provided in the window pocket between the window and a wall of the window pocket. A light-source bracket that may be provided at a side of the nozzle pipe which may be opposite to a side of the nozzle pipe from which the liquid-supplying hose barb extends.

Embodiments disclosed herein may be implemented as a liquid dispenser comprising a pipe extending in a first direction and having a first passage, a hose barb extending in a second direction which may be inclined with respect to the first direction, the hose barb having a second passage, an elbow to connect the hose barb and the nozzle pipe, wherein the elbow and hose barb are configured such that a center axis of the second passage does not intersect with a center axis of the first passage, and a frame having a third passage provided above and communicating with the first passage. The frame may be configured to receive a lens in the third passage.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A liquid dispenser, comprising:
    a nozzle pipe including a first section having a first passage and a second section having a second passage communicating with the first passage, wherein the second passage has a cylindrical shape with a diameter smaller than a diameter of the first passage;
    a window pocket provided above the first section of the nozzle pipe;
    a light source provided above the widow pocket and configured to emit ultraviolet light into the first passage;
    a window provided in the window pocket to be between the first passage and the light source;
    an elbow branched from the first section of the nozzle pipe at an inclination with respect to the nozzle pipe;
    a liquid-supplying hose barb extending from the elbow at the inclination; and
    a hose coupled to the liquid-supplying house barb,
    wherein a center axis of the first section of the nozzle pipe does not intersect with a center axis of the liquid-supplying hose barb such that liquid discharged from the elbow and entering the liquid-supplying hose barb flows along the first section of the nozzle pipe in a swirling flow.

2. The liquid dispenser of claim 1, wherein a central axis of the liquid-supplying hose barb is positioned to pass outside of an inner area of the nozzle pipe.

3. The liquid dispenser of claim 1, wherein the elbow is configured to connect with the nozzle pipe to contact an outer surface of the nozzle pipe.

4. The liquid dispenser of claim 1, further comprising a laminar flow protrusion provided in the second passage and protruding inward from an inner surface of the second section toward a center of the second passage, the laminar flow protrusion extending in an axial direction of the second passage.

5. The liquid dispenser of claim 1, wherein an inner surface of the liquid-supplying hose barb and an inner surface of the nozzle pipe are coated with aluminum.

6. The liquid dispenser of claim 1, further comprising a seal provided in the window pocket between the window and a wall of the window pocket.

7. The liquid dispenser of claim 1, further comprising a light-source bracket that is provided at a side of the nozzle pipe which is opposite to a side of the nozzle pipe from which the liquid-supplying hose barb extends.

8. The liquid dispenser of claim 1, wherein an inner space of the elbow communicates with the nozzle pipe such that a central axis of the elbow passes through an inner area of the nozzle pipe.

9. The liquid dispenser of claim 8, wherein the liquid-supplying hose barb is inclined with respect to a plane which is perpendicular to a central axis of the nozzle pipe.

10. The liquid dispenser of claim 9, wherein:
    the nozzle pipe includes a first end which receives liquid and a second end through which the liquid is discharged, and
    the first passage has an inner diameter which becomes narrower in a direction from the first end of the nozzle pipe toward the second end of the nozzle pipe.

11. A liquid dispenser, comprising:
    a pipe extending in a first direction and having a first passage;
    a hose barb extending in a second direction which is inclined with respect to the first direction, the hose barb having a second passage;
    an elbow to connect the hose barb and the nozzle pipe, wherein the elbow and hose barb are configured such that a center axis of the second passage does not intersect with a center axis of the first passage; and
    a frame having a third passage provided above and communicating with the first passage, wherein the frame is configured to receive a lens in the third passage.

* * * * *